(12) United States Patent
Pusch et al.

(10) Patent No.: US 10,517,743 B2
(45) Date of Patent: Dec. 31, 2019

(54) METHOD FOR CONTROLLING AN ORTHOPEDIC JOINT DEVICE

(71) Applicant: OTTO BOCK HEALTHCARE GMBH, Duderstadt (DE)

(72) Inventors: Martin Pusch, Duderstadt (DE); Christian Will, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/412,418

(22) PCT Filed: Jul. 3, 2013

(86) PCT No.: PCT/EP2013/001957
§ 371 (c)(1),
(2) Date: Dec. 31, 2014

(87) PCT Pub. No.: WO2014/005709
PCT Pub. Date: Jan. 9, 2014

(65) Prior Publication Data
US 2015/0150694 A1    Jun. 4, 2015

(30) Foreign Application Priority Data

Jul. 3, 2012   (DE) .................. 10 2012 013 140

(51) Int. Cl.
*A61F 2/60* (2006.01)
*A61F 2/74* (2006.01)
(Continued)

(52) U.S. Cl.
CPC ............... *A61F 2/605* (2013.01); *A61F 2/60* (2013.01); *A61F 2/64* (2013.01); *A61F 2/66* (2013.01);
(Continued)

(58) Field of Classification Search
CPC ...... A61F 2/60; A61F 2/604; A61F 2/64–646; A61F 2/68
See application file for complete search history.

(56) References Cited

U.S. PATENT DOCUMENTS 4,051,558 A * 10/1977 Vallotton ............... A61F 2/604
  623/26
4,911,709 A *  3/1990 Marlow ................. A61F 2/644
  623/39

(Continued)

FOREIGN PATENT DOCUMENTS

DE   102008045113 A1   3/2010
DE   102008045113 B4   8/2011
(Continued)

OTHER PUBLICATIONS

Machine Version of English Translation for Mosler DE 10 2008 045113 A1; Apr. 3, 2010.*

(Continued)

*Primary Examiner* — Marcia L Watkins
(74) *Attorney, Agent, or Firm* — Holland & Hart, LLP

(57) ABSTRACT

A method for controlling an orthopaedic joint device of a lower extremity. The joint device has an upper part and a lower part mounted in a hinged manner on the latter. Arranged between the upper part and the lower part is an energy converter by which, during walking, kinetic energy from the relative movement between the lower part and the upper part is converted or stored and supplied again to the joint in order to support the relative movement, wherein kinetic energy within one movement cycle is converted and/or stored and, within the same movement cycle, is supplied again as kinetic energy to the joint device in a controlled manner and staggered in time.

10 Claims, 15 Drawing Sheets

(51) Int. Cl.
    *A61F 2/68*     (2006.01)
    *A61F 2/70*     (2006.01)
    *A61F 2/64*     (2006.01)
    *A61F 2/66*     (2006.01)
    *A61F 2/50*     (2006.01)

(52) U.S. Cl.
    CPC . *A61F 2002/503* (2013.01); *A61F 2002/5006* (2013.01); *A61F 2002/5032* (2013.01); *A61F 2002/5033* (2013.01); *A61F 2002/5035* (2013.01); *A61F 2002/5043* (2013.01); *A61F 2002/5072* (2013.01); *A61F 2002/6818* (2013.01); *A61F 2002/6845* (2013.01); *A61F 2002/701* (2013.01); *A61F 2002/704* (2013.01); *A61F 2002/708* (2013.01); *A61F 2002/741* (2013.01); *A61F 2002/745* (2013.01); *A61F 2002/748* (2013.01)

(56) References Cited

U.S. PATENT DOCUMENTS

| | | | |
|---|---|---|---|
| 5,181,931 A | | 1/1993 | van de Veen |
| 5,571,205 A | * | 11/1996 | James .................... A61F 2/64 623/24 |
| 6,113,642 A | * | 9/2000 | Petrofsky ................ A61F 2/68 188/282.3 |
| 6,613,097 B1 | * | 9/2003 | Cooper .................... A61F 2/68 623/39 |
| 7,963,998 B2 | * | 6/2011 | Boiten .................... A61F 2/605 623/43 |
| 8,974,543 B2 | | 3/2015 | Balboni et al. |
| 2006/0249315 A1 | | 11/2006 | Herr et al. |
| 2007/0233279 A1 | | 10/2007 | Kazerooni et al. |
| 2010/0023133 A1 | | 1/2010 | Fairbanks et al. |
| 2010/0038983 A1 | | 2/2010 | Bhugra et al. |
| 2011/0098828 A1 | | 4/2011 | Balboni et al. |
| 2013/0150980 A1 | * | 6/2013 | Swift ...................... A61F 2/68 623/24 |

FOREIGN PATENT DOCUMENTS

| | | |
|---|---|---|
| EP | 0439028 B1 | 5/1994 |
| EP | 1417942 A2 | 5/2004 |
| EP | 1991180 B1 | 9/2012 |
| JP | 2009-528077 | 8/2009 |
| JP | 2011-092507 | 5/2011 |
| JP | 2011-518633 | 6/2011 |
| WO | WO 01/17466 A2 * | 3/2001 |
| WO | 2007025116 A2 | 8/2006 |
| WO | 2007103579 A2 | 9/2007 |
| WO | 2010064063 A1 | 6/2010 |

OTHER PUBLICATIONS

PCT International Search Report for PCT International Patent Application No. PCT/EP2013/001957, dated Jan. 21, 2014.

\* cited by examiner

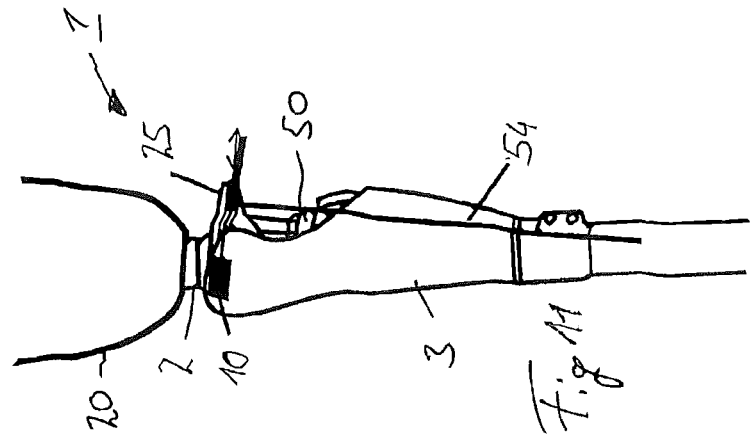
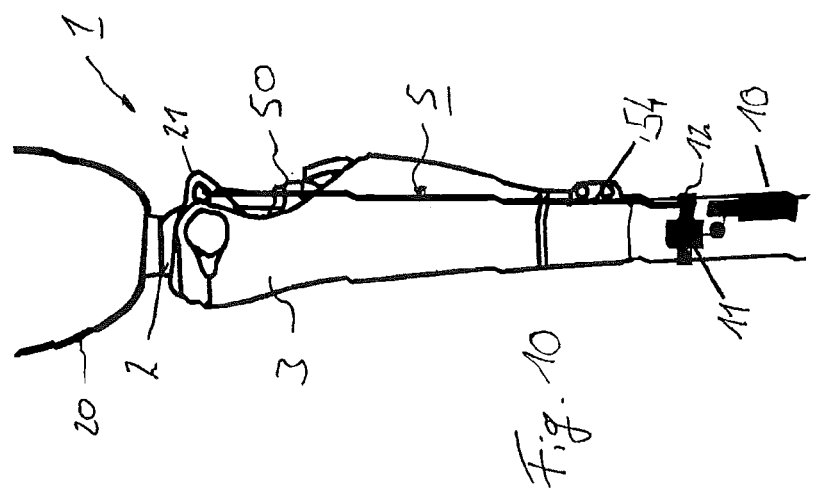

METHOD FOR CONTROLLING AN ORTHOPEDIC JOINT DEVICE

TECHNICAL FIELD

The invention relates to a method for controlling an orthopedic joint device of a lower extremity and also to an orthopedic joint device as such; the joint device has an upper part and a lower part mounted in an articulated manner thereon; arranged between the upper part and the lower part is a damping device, by way of which the extension damping and/or the flexion damping of the pivoting movement is brought about, kinetic energy from the relative movement between the lower part and the upper part being converted and stored and fed back to the joint during the walking in order to assist the relative movement.

BACKGROUND

Orthopedic joint devices of a lower extremity are for example orthoses or prostheses. In particular in the case of prostheses, which replace a natural knee joint, it is advantageous and intended that active influencing of the flexion and extension resistance takes place in the course of the movement cycle, in order to adapt the behavior of the joint device to the movement behavior or to other influences.

In addition, there are motor-driven prostheses or orthoses, the drive motors of which serve the purpose of executing a flexion or extension of the respective joint device.

WO 2007/025116 A2 describes a prosthetic device with an electronically controlled prosthetic knee with a regenerative braking device. In certain situations, the kinetic energy that exists during walking is converted into electrical energy and stored. In other situations it is provided that the gait is assisted or completely controlled. An electronic control system is provided in order to control the operation of the prosthetic device and distribute electrical energy that is generated. Excess electrical energy can be stored in a storage battery or capacitor and called upon for movement assistance at a suitable point in time. The energy storage devices in the case of prostheses or orthoses are large and heavy, in order to have adequate capacity to allow effective movement assistance to take place. In addition, there is the possibility that the active displacement of the upper part in relation to the lower part by correspondingly powerful drives brings the user into situations over which he or she no longer has control.

EP 439 028 B1 describes a swivel connection between two parts of an orthopedic aid in the form of a polycentric prosthetic knee joint, in the case of which a link member is designed to be variable in length under the effect of an external force. The changing of the length of the link member may be of a spring-elastic form, so that the link member resumes its original length immediately after the external force is reduced or ceases.

SUMMARY

The object of the present invention is therefore to provide a method and a device with which it is possible to achieve an improvement of the gait pattern without the user being put at risk and having to bear a heavy joint device.

This object is achieved according to the invention by a method with the features of the main claim and an orthopedic joint device with the features of the alternative independent claim. Advantageous configurations and developments of the invention are presented in the respectively dependent subclaims, the description and the figures.

The method according to the invention for controlling an orthopedic device of a lower extremity, in the case of which the joint device has an upper part and a lower part mounted in an articulated manner thereon and between the upper part and the lower part there is arranged an energy conversion device, by way of which kinetic energy from the relative movement between the lower part and the upper part is converted and/or stored and fed back to the joint during the walking in order to assist the relative movement, provides that, within a movement cycle, kinetic energy is converted and/or stored and, within the same movement cycle, is fed back to the joint device after a time delay as kinetic energy. In a typical movement cycle of an orthopedic joint device of a lower extremity, that is to say in a typical stepping cycle, there are phases in which excess energy has to be converted, but also phases in which assistance with kinetic energy is appropriate. It is therefore provided that excess energy that is stored or converted and stored for decelerating a component of the joint device is fed back at a suitable point in the same stepping cycle, there being a time delay between the storing or converting and storing and the renewed supplying as kinetic energy, that is to say the return does not follow on immediately after the storage. On account of the supplying of the converted or stored energy in the same movement cycle, a large storage battery or capacitor is unnecessary, since there are only relatively small amounts of energy. As a result, weight is saved and the joint device can be kept lightweight. The device for converting and/or storing kinetic energy may be formed as part of a damper device and bring about part of the extension damping and/or the flexion damping of the pivoting movement when energy is converted or stored. The device may be designed as a hydraulic damper and/or a pneumatic damper; likewise, a configuration as a generator may be provided.

Combinations of the devices described above with one another are also possible. The device for converting and/or storing kinetic energy may be provided along with conventional damper devices. The other damping components, generally pneumatic or hydraulic dampers, continue to be retained, but either an energy store or a generator that can be switched over to operate as a motor is additionally provided in order to take kinetic energy from the system or supply it to the system at the suitable points within the movement. On account of the fact that the hydraulic or pneumatic damping system dissipates a large proportion of the energy, the system for assisting the movement can be kept small and lightweight. The point in time of the energy conversion and return is established by way of a control device.

A development of the invention provides that kinetic energy is converted and/or stored during an extension movement. The renewed supplying of kinetic energy may take place in the initiation of the swinging phase to assist the swinging phase flexion. Likewise, kinetic energy may be fed back after the lifting off of the toe ("toe off") during the step to maintain the flexion velocity. It is also provided that, after reaching the maximum flexion angle, which may be ascertained for example through a reversal of movement or by a velocity sensor, energy is supplied to assist the extension movement. Renewed supplying of the kinetic energy may also take place after the flexion movement following the initial heel contact, that is to say the standing phase flexion, to assist the extension movement. It is possible in principle that the supplying only takes place in a single phase of the stepping movement; as an alternative to that, supplying of kinetic energy may take place at a number of phases or all the phases described or points in time of the stepping movement.

Furthermore, it may be provided that kinetic energy is converted and/or stored during the flexion movement and is fed back for initiating the swinging phase to assist the flexion movement and/or to maintain the bending velocity after the lifting off of the toe. It may therefore be provided that the kinetic energy is converted and/or stored after initiation of the swinging phase and is only fed back to assist the bending movement after reaching the maximum flexion velocity. The reaching of the maximum flexion velocity may be ascertained by a velocity sensor or an acceleration sensor.

The extension movement is generally decelerated before reaching the maximum extension, in order to reduce the impulse that there is when striking against the extension limit stop occurs without deceleration. This kinetic energy may be converted and/or stored and fed back for initiating and/or assisting the flexion of the joint device. During the swinging phase of the joint device, kinetic energy can be supplied to increase or maintain the extension velocity, in order to facilitate and assist the forward extension of the lower part.

It is also provided that kinetic energy is converted and/or stored during the standing phase at the beginning of the standing phase flexion with heel loading, before reaching the extension stop limit and/or after initiating the standing phase flexion with forefoot loading. In particular, the kinetic energy may be converted and/or stored with the initial heel impact and fed back for initiating and/or assisting the flexion movement after reaching an extension stop limit.

With increasing walking speed, it may be provided that less kinetic energy is supplied to the joint, in order not to boost the system itself and thereby make the user of the orthopedic joint device walk faster and faster.

The kinetic energy may be converted into electrical energy and buffer-stored or converted into potential energy and buffer-stored, for example by charging an energy store, for example a spring or a hydraulic or pneumatic pressure accumulator.

It is also provided that the converted energy is completely fed back to the joint device in one movement cycle, so that there is no storage of the converted energy beyond the movement cycle. As a result, it is ensured that only the energy that exists and is converted during the one movement cycle can be fed back to the system as kinetic energy. This may take place by providing that, after the detected return of a characteristic variable of the movement cycle, the energy stored until then is dissipated or the amount of energy over the last movement cycle is continually checked.

Furthermore, it may be provided that the storage and/or conversion of the kinetic energy is only carried out in predetermined phases during a movement cycle, that is to say that the energy conversion device does not work constantly to convert part of the kinetic energy from the movement, store it or feed it back to the joint device as kinetic energy. For this purpose, either certain movement phases in which conversion, storage or return always take place, for example by way of a mechanical or electrical control device, are established or the points in time and time periods in which conversion, storage or return take place are established on the basis of an analysis of the movement from characteristic variables for each movement cycle or for a predetermined or calculated number of movement cycles. This may take place for example by way of an electronic control device.

A development of the method according to the invention in which, during pivoting of the upper part in relation to the lower part, mechanical work from the relative movement is converted and stored in at least one energy store and fed back to the joint device after a time delay, in order to assist the relative movement, provides that the stored energy is converted back and the supply of mechanical work for and during the assistance of the relative movement takes place in a controlled manner. When energy is released from an energy store, for example a spring, according to the prior art the stored energy is supplied to the joint device, that is to say the system comprising the upper part and the lower part and the articulated mounting, as a sudden surge, so that a great amount of energy is introduced over a very short time period. It is provided that the stored energy is fed back to the system, and converted into mechanical work and assistance for the displacement of the upper part in relation to the lower part, in a controlled manner, in order to assist the movement over a longer time period, so that a movement of the prosthetic or orthotic device that is approximated to the natural sequence of movements can take place. According to the prior art, an adaptation to changed gait patterns, the speeds or different patients can only be carried out with extremely great effort, in that specifically adapted springs are used, which is impractical for daily use. According to the invention, on the other hand, the energy released into the system is checked, so that the required amount of energy can be fed in over a comparatively long time period, in order to influence the gait pattern as desired.

The supply of the mechanical work can be changed by energy being externally supplied to or drawn from the energy store. If the energy store is a spring, the supply of energy may take place by the spring being retensioned; the drawing or reducing of the amount of energy may take place by the spring being relaxed, for example by displacement of a spring abutment. If the energy store is designed as an electrical energy store, for example a capacitor, battery or storage battery, the changing of the amount of energy may take place by activation of a generator or introduction from a second energy store; the reduction of the amount of energy may take place by connecting a load or diversion into a second store for electrical energy.

A development of the invention provides that the energy store is assigned an actuator, by way of which the energy store is filled or brought to a minimum level if the relative movement is not sufficient for this. Should the energy that is available as a result of the movement not be sufficient to supply the energy store with sufficient energy for the next step or the sequence of movements, the minimum amount depending on the walking speed, the walking situation and the individual circumstances of a patient, it is provided according to the invention that, during the walking and before the return of energy for assisting the relative movement, the energy store is filled up to a fixed level, for example by compressing a spring or by driving a generator that charges the electrical energy store.

In order to be able to determine precisely the point in time of the movement assistance, it is provided according to the invention that the energy store is assigned a releasing device, by way of which the energy is partially or completely released from the energy store. The releasing device determines the point in time of the release of energy; in the case of complete release, the duration and the progression of the release of energy is not controlled by way of the releasing device, but by way of changes in the energy store, that is to say drawing or supplying energy. In the case of a partial release, a reduction of the amount of energy released takes place, so that the initial level of the movement assistance can be set. A partial release allows an adaptation for example to walking speeds, patients or walking situations to be performed; the fine influencing of the assistance takes place by way of the changing in the energy store.

The energy may be supplied as mechanical work in dependence on at least one following criterion or a combination of a number of the following criteria, to be specific the angular position of the upper part in relation to the lower part, the position of the upper part and/or the lower part in space, an angular velocity of the upper part and/or the lower part, the relative velocity between the upper part and the lower part, the loading situation and/or the acceleration of the upper part and/or the lower part. As a result, it is possible that assistance of the movement that is as exact as possible in terms of time and amount takes place. The positions of the upper parts and lower parts in relation to one another and in space can be determined by angle sensors or inertial sensors, the velocities in relation to one another or within space by acceleration sensors or a combination of angle sensor and acceleration sensor. The sensors can be used not only for determining the point in time of the release of energy, but also for determining the respective walking situation, the walking speed and the current position of the respective components in relation to one another or in space, thereby making it possible to determine and control the amount and the progression of the supply of energy for assisting the movement.

A development of the invention provides that the energy is fed to or drawn from the energy store in dependence on at least one or more of the criteria presented above, in order to carry out the checked control of the movement.

The point in time of the intervention of the conversion device for changing the amount of energy to be converted and/or the amount of energy supplied can be adjusted, so that for example it can be set in dependence on the walking speed, the walking situation or the individual parameters of the patient, how large the amount of energy to be stored is or how large the amount of energy to be released must be. In the case of a desired large amount of energy, it is provided that the earliest possible intervention in the conversion takes place, so that for example a generator is driven very early and for a very long time, or a spring is precompressed very far, in order to convert the mechanical work when walking, for example when the heel touches down in standing phase flexion, to the maximum extent into the potential energy of a spring or electrical energy of a storage battery or a capacitor. If the point in time of the intervention in the conversion back is adjusted, for example by displacement of a limit stop or an angle-dependent release, the energy is introduced at a later point in time of the step, whereby changing of the gait pattern can be achieved. The energy store may be charged by an actuator if the conversion device is not active on account of the relative movement between the upper part and the lower part, so that the actuator does not have to work against the relative movement. In addition, arranging the timing of the charging of the energy store by the actuator in a phase in which no mechanical work from the joint device is converted has the advantage that energy can be stored over a long time period, which has the result that the actuator can be made to correspondingly small dimensions, to allow the desired amount to be provided over a great time period. If, for example, a spring is compressed by way of a motor as an actuator, the motor may be of a small design and be coupled by a transmission to the spring, so that the spring can be compressed over a comparatively great time period. The same applies to the conversion and storage of electrical energy.

A development of the invention provides that, in addition to influencing the energy store, the relative movement is influenced by way of a damping device, so that the control does not have to take place exclusively by way of the energy store, which has the result that there is a great possibility for variation in the influencing of the gait pattern. In addition, loading peaks can be absorbed more easily by way of an additional damper device.

The orthopedic joint device of the lower extremity with an upper part and a lower part mounted in an articulated manner thereon and a device for converting and/or storing kinetic energy provides that the storage device has a rate of conversion and/or storage that is inversely proportional to the pivoting velocity of the lower part in relation to the upper part. As a result, it is ensured that, in spite of the actually increasing kinetic energy to be converted, no self-boosting takes place, so that the system of the joint device remains stable.

A generator for generating electrical energy and a motor for driving the lower part may be provided, the generator being preceded by a speed-dependent coupling, which connects the generator to a drive device. The greater the speed of movement, the lower the power that has to be transmitted by way of the coupling, so that the inverse proportionality of the energy generation in relation to the pivoting velocity is realized by way of the coupling.

A hydraulic damper unit for damping the pivoting movement may be arranged between the lower part and the upper part in the joint device, the hydraulic fluid of the hydraulic damper unit serving as an actuator for separating the coupling. The coupling may be designed as a speed-dependent slip clutch.

A flywheel or a pressure accumulator may be provided as the storage device for the kinetic energy. The joint device is preferably designed as a hip joint, knee joint or foot joint of a prosthesis or an orthosis. The energy store may also be designed as a spring or storage battery, a storage battery also being understood as meaning a capacitor or a rechargeable battery.

A development of the orthopedic joint device provides that the energy store is assigned an actuator, which supplies or draws energy to or from the energy store in a controlled manner during the assistance of the relative movement. The controlled supplying or controlled drawing of energy to or from the energy store by way of an actuator makes it possible to influence the gait pattern particularly easily and reliably in the case of semiactive joint devices, in particular in the case of semiactive prosthetic knee joints. The conversion device may be designed as a spring or generator, in order to store the mechanical work that occurs during a relative movement between the upper part and the lower part either as potential energy in a spring or electrical energy in an electrical storage device, for example in the form of a storage battery, in a rechargeable battery or in a capacitor.

A separate damper device may be arranged between the upper part and the lower part, in order to be able to keep a better check on the relative movement with assistance by the energy store. By superposing the influencing of the energy store with the separate damper device, more precise and more reliable influencing of the gait pattern can take place. The damper device may be of an adjustable design, in order to provide adapted damping in dependence on sensor data, for example with respect to the joint angle, the walking speed, an angular velocity or an absolute angle of an upper part and/or a lower part. The damper device may be adjusted by way of an actuator in order to achieve a reduction or increase of the damping.

The conversion device may be adjustably coupled to the upper part and/or to the lower part in order to displace a position of intervention or a path of adjustment. As a result, it is possible to influence both the amount of energy and the point in time of the supply of energy as desired.

With the method described and the device described it is possible that the required energy is supplied only at a suitable point during the sequence of movements and in a minimal amount. The user of the orthopedic device continues to introduce the greatest part of the kinetic energy, for example by way of the remaining stump. However, a supply of energy is necessary, or at least advantageous, at two points at which the user of the joint device cannot introduce the required energy by physical exertion, for example because the physical strength is not sufficient if very high accelerations are required because of the mass moments of inertia. Thus, for example, assistance in the swinging phase when swinging over the ground is advisable, in order to prevent the lower part from dragging on the ground during walking. Selective supplying of energy allows the knee angle to be increased, so that greater ground clearance is realized. In the case of alternating climbing up stairs, an additional extension moment can enable the user to use his or her own strength to overcome the rest of the step.

On the basis of the fact that it is only ever the minimum-necessary amounts of energy that are fed as kinetic energy into the system, the user retains control over the orthopedic device at all times. The energy respectively stored would not be sufficient to bring the user into a critical situation. In addition, the occurrence of muscular deficits is avoided, since the user continues to have to apply the kinetic energy himself or herself; only the fine control is undertaken by the method or the device.

BRIEF DESCRIPTION OF THE DRAWINGS

Exemplary embodiments of the invention are explained in more detail on the basis of the accompanying figures, in which:

FIG. 10 shows a joint device with an elastic cord as an energy store;

FIG. 11 shows a variant of FIG. 1 with a displaceable spring attachment;

FIG. 17 shows a representation of a lever arm progression against a joint angle.

DETAILED DESCRIPTION

Figure 1:
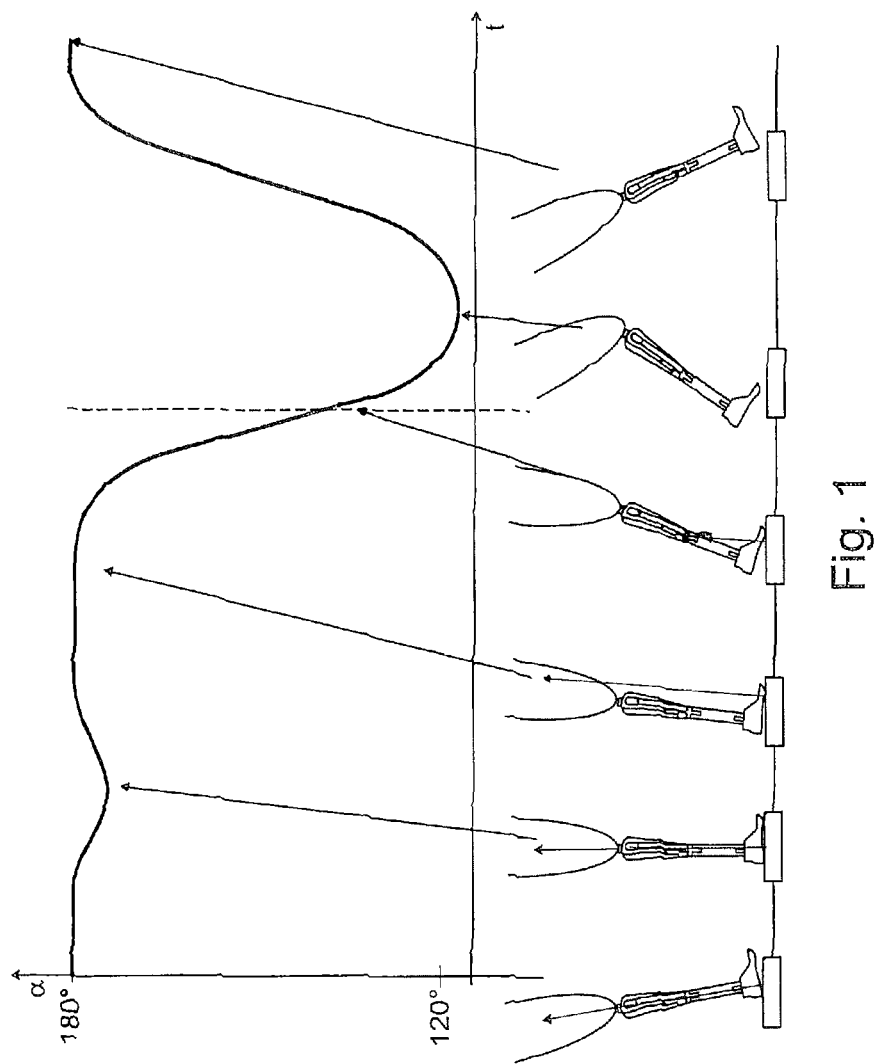
FIG. 1 shows a knee angle progression during a gait cycle.

In FIG. 1, a schematic representation of the progression of the knee angle $\alpha$ over time is shown. The representation comprises a gait cycle, that is to say beginning from the setting down of the heel up until the renewed setting down of the heel of the same leg. After the initial touching down of the heel with a stretched knee joint, that is to say at a knee angle $\alpha$ of 180°, the knee joint initially bends a little in the standing phase, which is referred to as standing phase flexion. As soon as the foot is set down completely on the ground, the knee joint is stretched, so that a knee angle $\alpha$ of 180° is established. In the course of the bending movement toward the end of the standing phase, the knee angle $\alpha$ decreases. The perpendicular, dashed line denotes the end of the standing phase, and consequently the point in time at which the tip of the foot leaves the ground. This point in time is known as "toe off". In the then-following swinging phase, the lower part swings further toward the rear and pivots in relation to the upper part up to the minimum knee angle $\alpha$ of 120°. There follows a reversal of movement; the lower leg with the prosthetic foot is brought forward and pivots up to the stretching stop limit, which lies at a knee angle $\alpha$ of 180°. In this stretched position, the touching down of the heel will generally take place.

Figure 2:
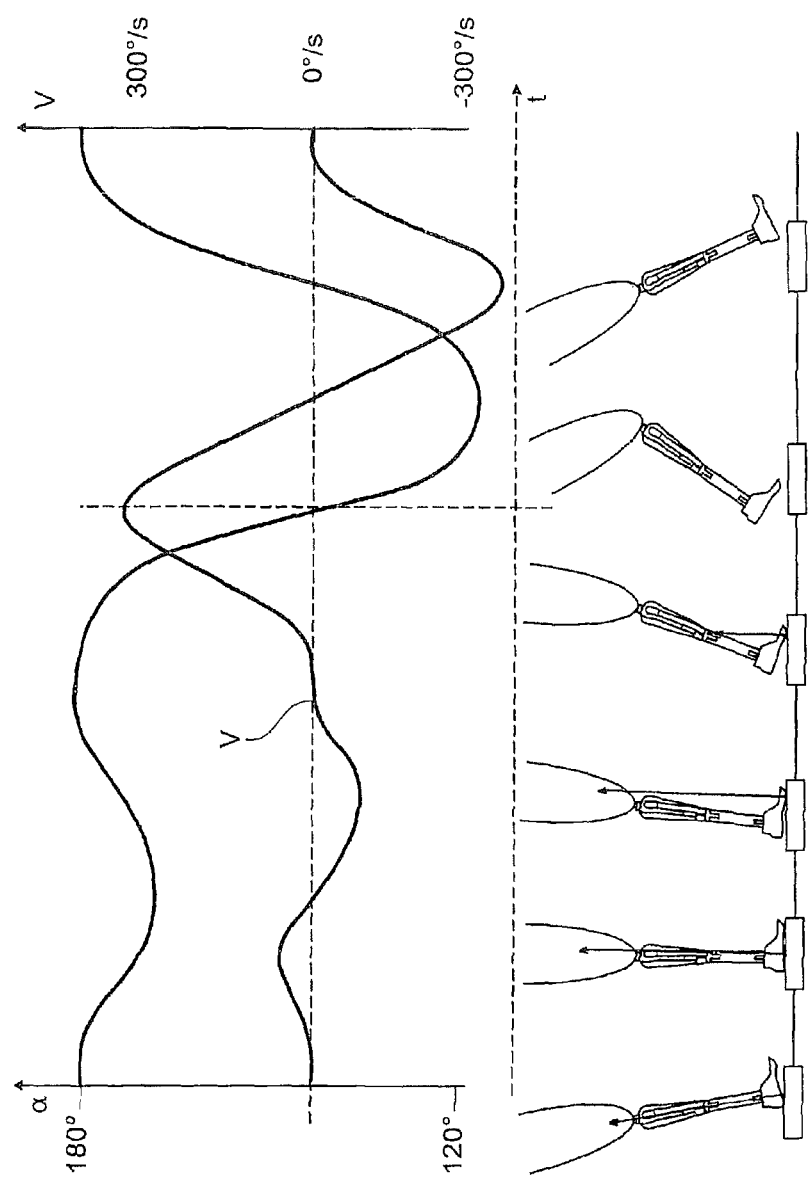
FIG. 2 shows the progression of the knee angle velocity over a gait cycle.

In FIG. 2, a schematic representation of the knee angle $\alpha$ is superposed with the knee angle velocity v. The knee angle profile corresponds in this case to that described in FIG. 1. During the initial standing phase flexion, the knee angle velocity v increases briefly. During the stretched phase, that is to say at a knee angle $\alpha$ of 180°, the knee angle does not change; likewise, the knee angle velocity v remains constant at 0° per second. The bending of the knee joint toward the end of the standing phase leads to a rise in the knee angle velocity v up to a maximum at the "toe off". The further swinging-back movement of the lower part takes place with a slowing speed, until at a minimum knee angle $\alpha$ a reversal of movement commences and the lower part executes an extension movement. Accordingly, the knee angle velocity extends below the zero line up to the point in time at which extension damping commences, in order not to allow the lower part to swing into the stretching stop limit without deceleration. Accordingly, the knee angle velocity v is reduced until the lower part has reached the stretching stop limit and the knee angle $\alpha$ is again 180°. The knee angle velocity v is then 0.

Figure 3:
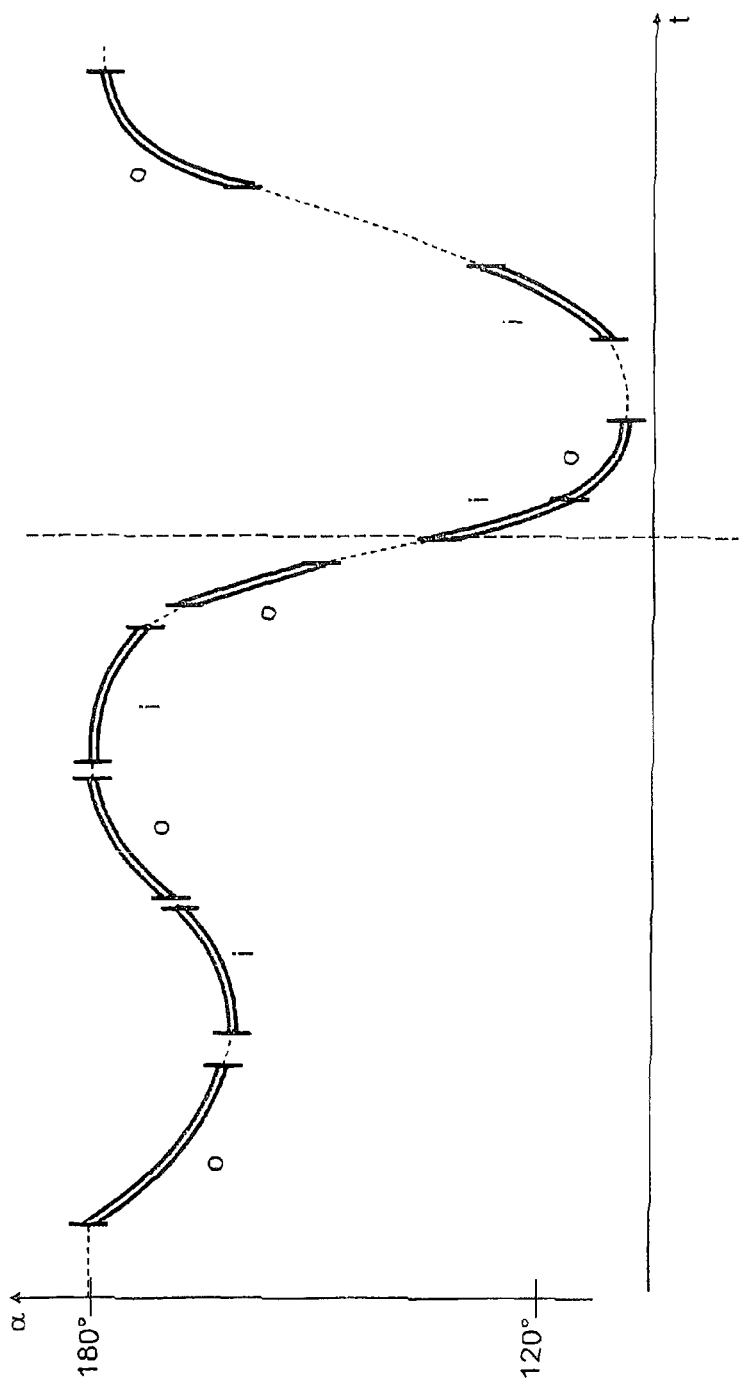
FIG. 3 shows phases of possible take-ups and releases of energy of the knee joint during the gait cycle.

In order to enter the region of great knee bending more quickly, it is possible and necessary in certain portions of the gait cycle to increase the knee angle velocity, for example in order to facilitate swinging through of the leg. The maximum knee bending may in this case remain the same or else be increased, if there is extension assistance, in order that the lower leg is brought forward quickly enough. In FIG. 3, the knee angle $\alpha$ over time during a gait cycle is represented once again. In it, regions in which kinetic energy from the relative movement between the lower part and the upper part can be converted or stored are marked; these regions are provided with the reference sign o. Furthermore, regions in which it may be advantageous to supply stored energy once again to the system, in order to assist extension or flexion, are marked by the reference sign i. During the initial standing phase bending, kinetic energy can be taken up, in order to feed it back, for example in the extension phase then immediately following. It is likewise possible to buffer-store the energy taken up in the bending phase or else toward the end of the stretching phase to supply it once again during a further energy take-up phase, so that the lower part is for example flexed or extended more quickly, in order to achieve the effect that is respectively desired. The supplying of the converted or stored energy after a controlled time delay takes place within the same movement cycle during predetermined phases i, it being preferred to use deceleration phases to convert and/or store energy and acceleration phases to feed this energy back after a controlled time delay. The control preferably takes place electronically; in principle, however, mechanical control is also possible.

Provided as supplying phases i are, in particular, the extension movement after the initial heel contact, the assistance of the bending to initiate the swinging phase, the maintenance of the flexion velocity after the "toe off" and also the assistance of the flexion movement after reaching the maximum flexion angle.

Figure 4:
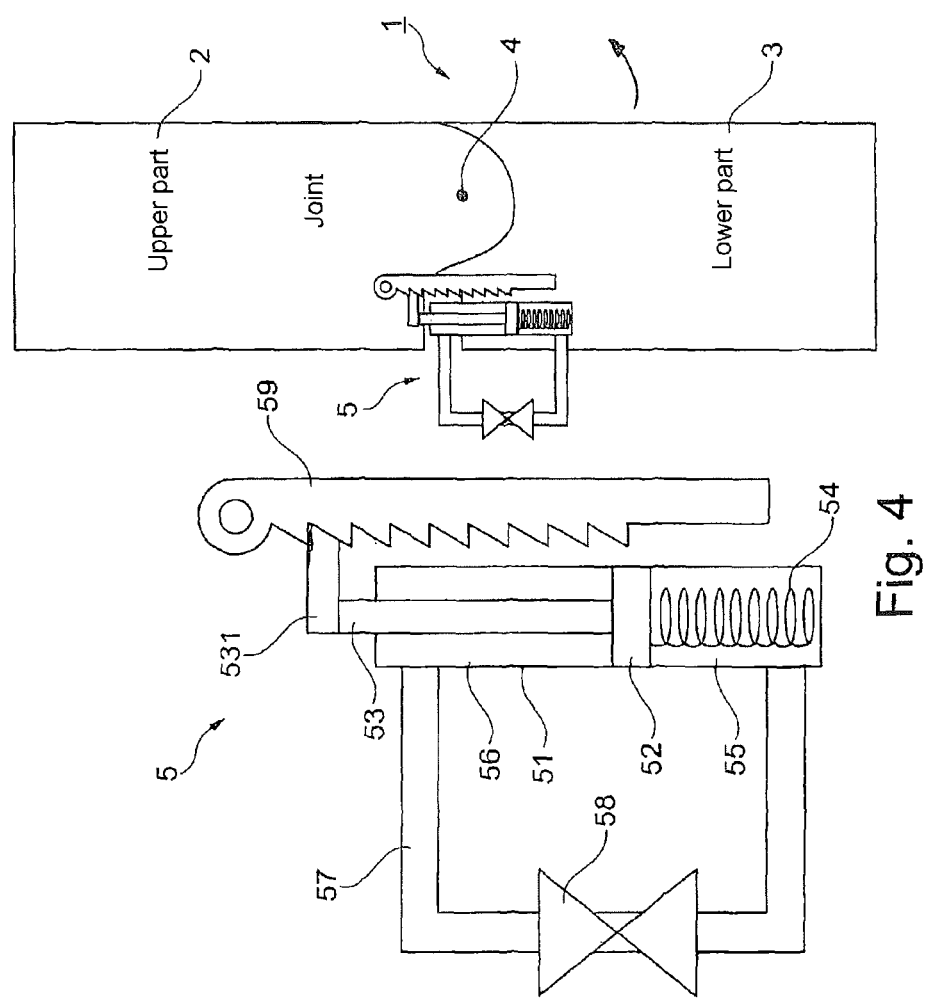
FIG. 4 shows a schematic representation of a joint device with an energy storage device for flexion assistance.

In FIG. 4, an example of an orthopedic joint device 1 is shown in a schematic representation. The orthopedic joint device 1 has an upper part 2 and a lower part 3. The lower part 3 is mounted on the upper part 2 pivotably about a pivot axis 4. The flexion takes place in the direction of the arrow; an energy conversion device 5 is arranged on the extension side. The energy conversion device 5 has a hydraulic cylinder 51, in which a piston 52 is arranged on a piston rod 53. The piston 52 is used for separating two chambers 55, 56 hydraulically from one another. In the lower chamber 55 there is arranged a compression spring. The two chambers 55, 56 are coupled to one another by way of a hydraulic line 57. In the hydraulic line 57 there is arranged a controllable valve 58, by way of which the flow rate from the upper chamber 56 into the lower chamber 55 can be controlled. At the upper end of the piston rod 53 there is arranged a sawtooth-like beveled form-fitting element 531, which is in engagement with a pivotably mounted toothed rack 59, which likewise has toothing in the form of sawteeth formed so as to correspond to that of the form-fitting element 531. During an extension movement of the lower part 3 in relation to the upper part, the piston 52 is pushed in. In order to initiate flexion assistance, the valve 58 is opened to such an extent that the valve 58 allows a faster piston movement than the joint device. For compressing the spring 54, the piston rod 53 is pushed downward. This takes place during an extension movement of the lower part 53 in relation to the upper part. If the lower part 3 flexes in relation to the upper part 2, the teeth of the toothed rack 53 slide along on the bevel of the form-fitting element 531 on account of their orientation; during the extension of the lower part 3, the spring 54 is compressed, since sliding of the toothed rack 59 is not possible due to the substantially horizontal areas of contact. For flexion assistance, for example in the initiation of the swinging phase, that is to say with a relatively greatly bent lower part 3, the form-fitting element 531 is in engagement relatively far down on the toothed rack 59 and assists the movement of the lower part 3 in the direction of the arrow. For flexion assistance, the valve 58 is mechanically or electrically controlled in dependence on an ascertained joint angle position or mechanically or electrically controlled in dependence on a joint angle velocity. If the valve 58 is opened, the spring 54 can relax, since the hydraulic fluid can flow out of the upper piston chamber 56 through the hydraulic line 57 into the lower chamber 55.

Figure 5:
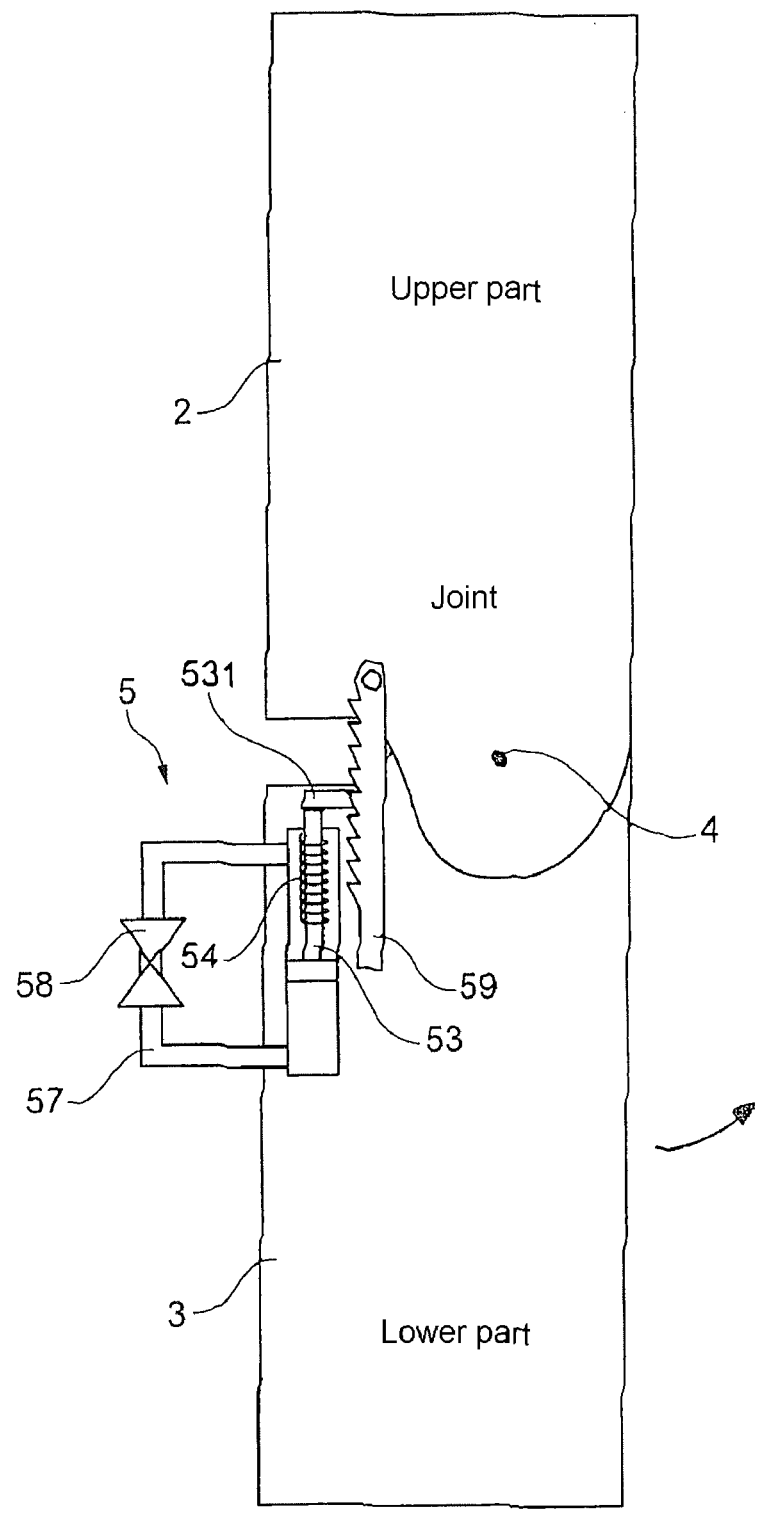
FIG. 5 shows a joint device with a device for extension assistance.

In FIG. 5 there is shown a joint device in which the direction of action is reversed in comparison with the embodiment according to FIG. 4. The spring 54 is arranged around the piston rod 53; the form-fitting element 531 and similarly the arrangement of the teeth in the toothed rack 59 are oriented in the opposite direction, so that there is extension assistance. The piston 52 is drawn out when there is flexion, and has an assisting effect for the extension when the valve 58 allows a piston movement, which the spring 54 assists. This may take place in particular when there is a reversal of the flexion movement into an extension movement. For controlling the assistance of the extension movement, the toothed rack 59 or ratchet may be mechanically decoupled or the valve 58 may intervene in a damping manner.

Figure 6:
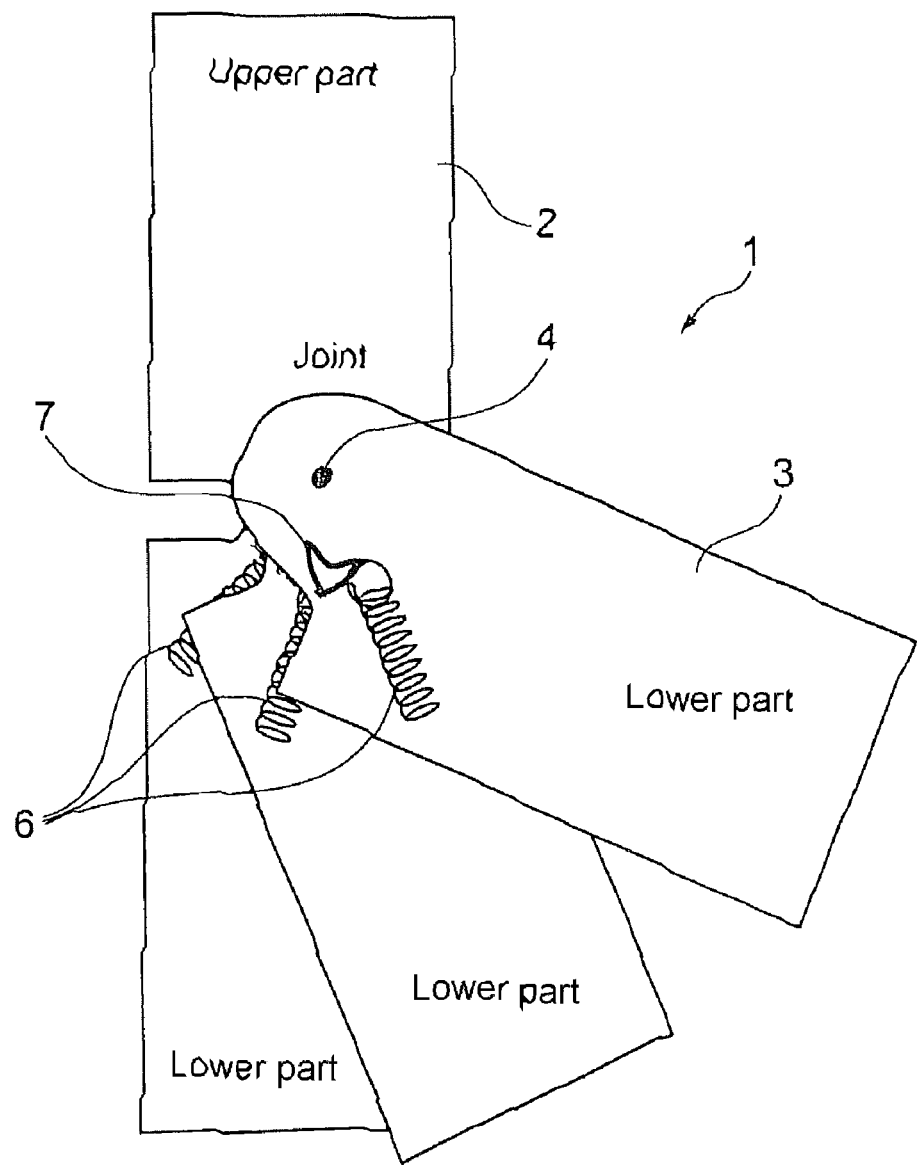
FIG. 6 shows a joint device with a spring mounted in a cam.

In FIG. 6, a further variant of the invention is represented, one in which a spring 6 is compressed by way of a cam 7 when there is flexion of the joint, in order to release the energy again when there is further bending. Consequently, kinetic energy can be stored during a flexion movement, for example during the heel strike, and be fed back to the joint device 1 for the initiation of the swinging phase for the assistance of the flexion movement and/or for the maintenance of the bending velocity after the "toe off". During the extension movement, the spring 6 remains ineffective on account of the guidance in the cam 7.

Figure 7:
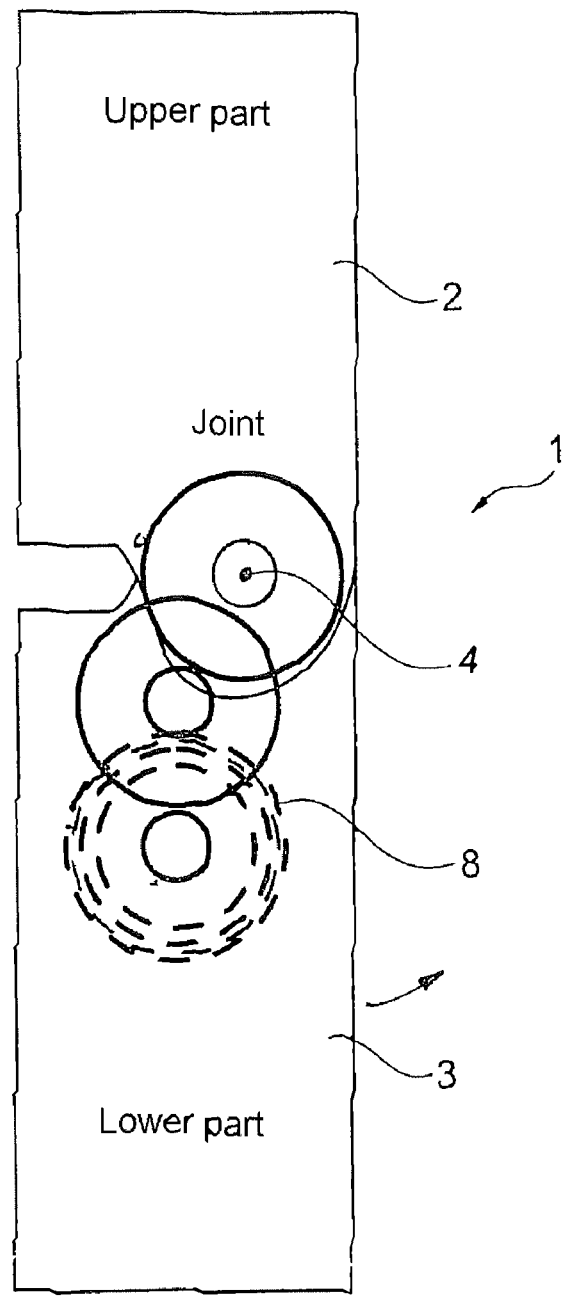
FIG. 7 shows a joint device with a flywheel mass as an energy store.

A further variant of the joint device 1 is shown in FIG. 7. In this case, a flywheel mass 8, which is accelerated when there is flexion of the lower part 3 in relation to the upper part 2, is provided as the device for converting and storing kinetic energy. As the flexion velocity slows down, the flywheel mass 8 releases the rotational energy again, so that, after reaching the maximum flexion velocity, that is to say after the "toe off", or the swinging through in the extension phase, energy is supplied to the joint device 1 to assist the respective movement.

Figure 8:
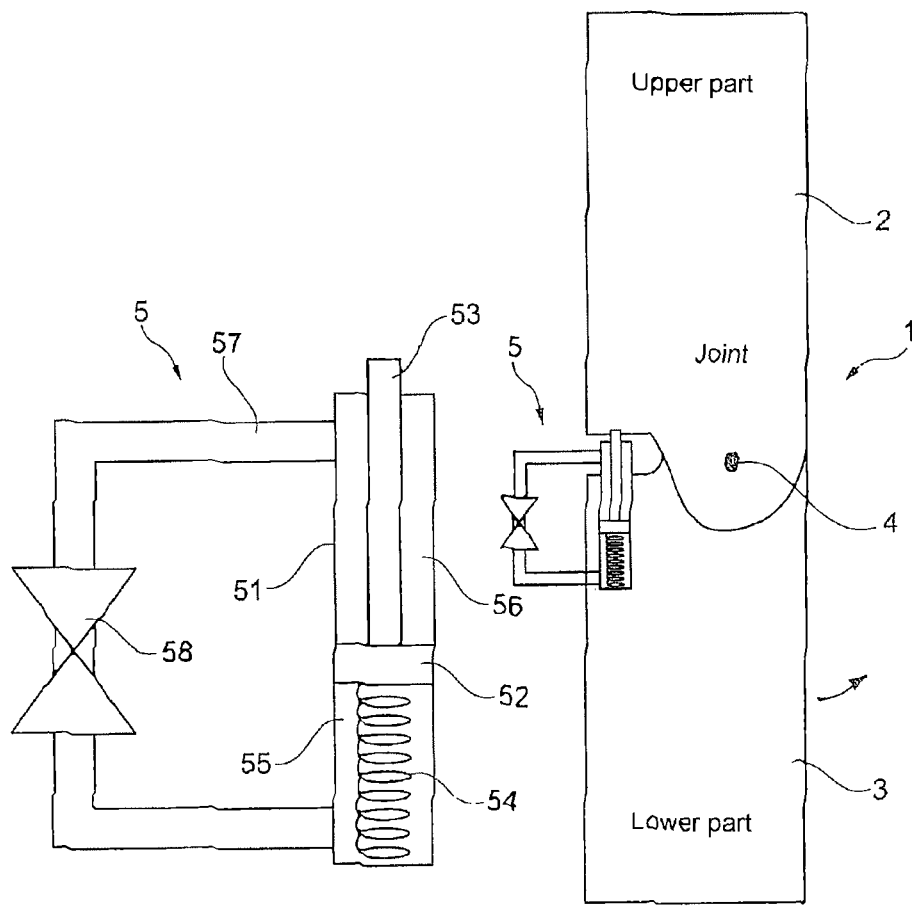
FIG. 8 shows a variant of the joint device with extension control.

In FIG. 8, the device 5 for converting and storing kinetic energy is constructed in a way similar to that described in FIG. 4, but without the form-fitting element 531 at the upper end of the piston rod 53 and without the toothed rack 59. With such a device it is possible to operate extension control, in particular to set the extension stop limit. If the joint device is stretched completely, the piston 52 is moved to the maximum extent into the lower chamber 55. The compression spring 54 is compressed to the maximum extent. The energy stored in this way can be released on opening of the valve 58 for flexion assistance, so that assistance is provided at the end of the standing phase for the initiation of flexion. The further the piston rod 53 is in this case moved out, the greater the knee angle α at which the extension control acts, since the upper end of the piston rod 53 or a component assigned to it comes into early contact with the stop surface in the upper part 2.

Figure 9:
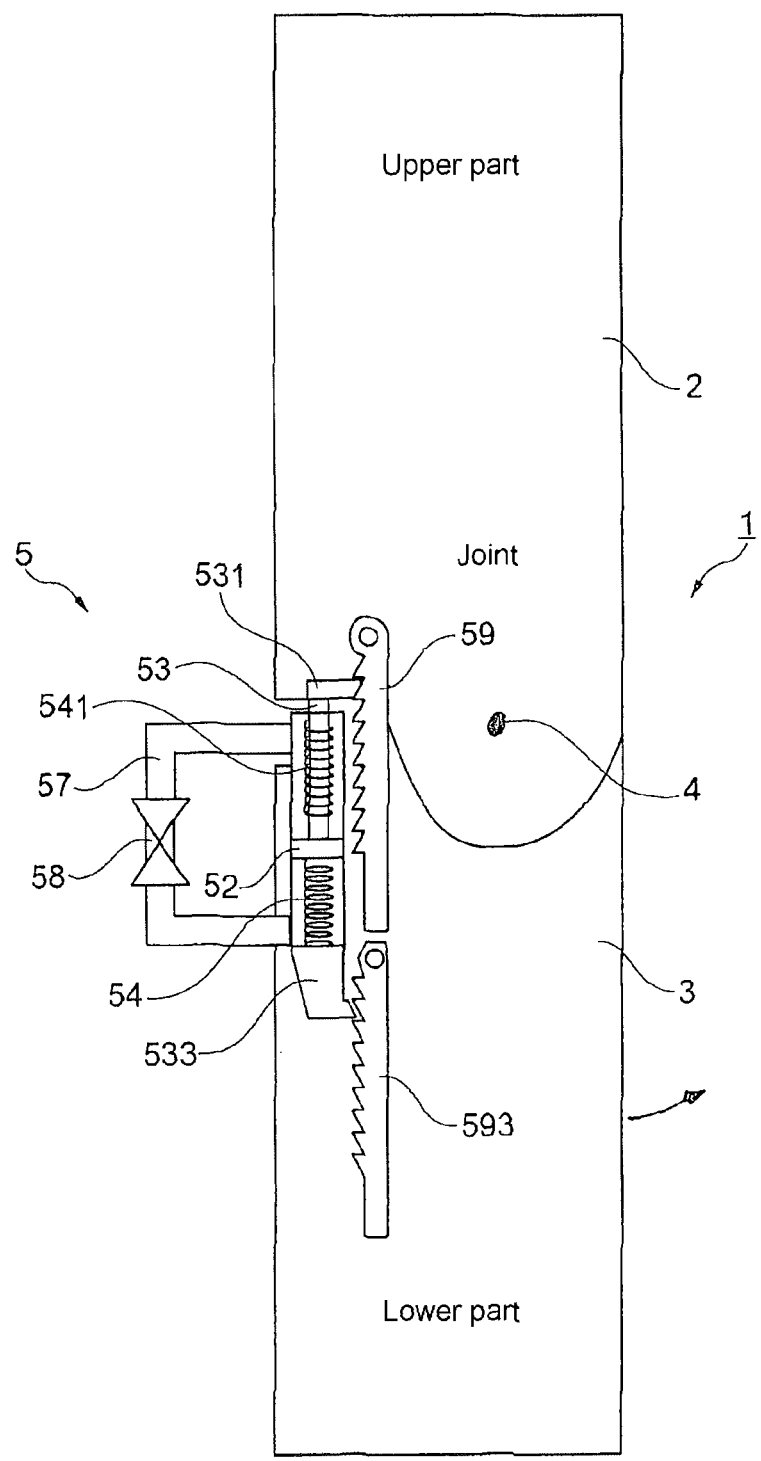
FIG. 9 shows a joint device with two springs.

In FIG. 9, a further variant of the invention is shown. In addition to the configuration according to FIG. 4, the energy conversion device 5 provides a second toothed rack 593 and a second form-fitting element 533. The second toothed rack 593 is arranged pivotably on the lower part 3; the second form-fitting element 533 acts on the spring 54 in the lower piston chamber 55. The piston 52 with the piston rod 53 is pushed in by way of the toothed rack 59 when there is extension. The spring 54 stores the kinetic energy as potential energy. Depending on the intended assistance, either the spring 541 on the piston rod or the spring 54 away from the piston rod is compressed.

The energy conversion device 5 may be assigned a speed-dependent coupling, which at increased knee angle velocities v provides reduced friction between force transmission elements, so that the rate of conversion or storage is inversely proportional to the pivoting velocity of the lower part 3 in relation to the upper part 2.

FIG. 10 shows an orthopedic joint device in the form of a prosthetic knee joint with an upper part 2, in which an upper leg shaft 20 for receiving an upper leg stump is arranged. A lower part 3 is fastened in an articulated manner distally in relation to the upper part 2, so that the upper part 2 can be pivoted in relation to the lower part 3. Formed on the rear of the upper part 2 is a bracket 21, arranged on which there is on the one hand a damper device 50 in the form of a hydraulic or pneumatic damper and on the other hand an energy store 54 in the form of an elastic cord. The elastic cord is connected by way of a transmission gear mechanism 11 to an actuator 10 in the form of an electric motor. The electric motor is arranged in a lower leg tube, which is fastened to the lower part 3. The energy store 5 in the form of the elastic cord is fastened to the transmission gear mechanism 11 and a bracket 12; if the motor 10 is activated, it acts by way of the transmission gear mechanism 11 on the bracket 12 and can either compress or relax the elastic cord 54, in that the bracket 12 is displaced in the distal or proximal direction or is turned in one direction or the other, in order to roll up or unroll the elastic cord. The bracket 12 consequently forms a displaceable mounting point of the energy store 5, whereby it is possible in the case of an extension movement of the lower part 3 to set the beginning of a tensioning operation of the elastic cord 54. The bracket 12 can be used to realize a displaceable, elastic stretching stop limit, which is adjusted by way of the actuator 10. The energy store 54, formed as a spring, is compressed by way of an extension movement of the lower part 3 and takes up part of the kinetic energy of the lower part 3. This may take place for example at the end of the swinging phase or after the heel strike and the standing phase flexion. The spring 54 is compressed in the course of the standing phase extension and continues to be kept compressed during the standing phase.

In the terminal standing phase, the stored energy can be released again to assist the initiation of the swinging phase; the elastic cord 54 is drawn in and converts the potential energy into mechanical work, in order to assist the flexion of the lower part 3. If more energy is to be stored in the energy store 54, the actuator 10 pretensions the elastic cord 54, in that the bracket 12 is displaced distally or in the rolling-up direction; if less energy is to be stored, the bracket 12 is displaced proximally or the cord is unrolled. In the exemplary embodiment represented, the energy storage device 54 is at the same time the conversion device 5, in which the mechanical work from the relative movement is converted into potential energy.

In addition to the conversion device 5 or the energy store 54, a separate damper 50 is provided in the form of a hydraulic or pneumatic damper, which is of an adjustable design, so that the damper device 50 can be used to influence the damping during walking, both in the direction of flexion and in the direction of extension.

For controlled assistance in the initiation of the swinging phase, it is provided that changing of the pretensioning of the elastic cord 54 takes place by way of the actuator 10, the transmission mechanism 11 and the displacement or turning of the bracket 12, in order to keep a better check on the release of energy. It has been found that a spring alone as the energy store has the effect of introducing too great a force too quickly, which can be perceived by the patients as unpleasant. In order to keep a check not only on the time period over which energy is introduced but also the amount of energy and the power output, a manipulation can be performed on the energy store 54 in dependence on the angular position of the upper part 2 in relation to the lower part 3, the angular position of the upper part 2 and/or the lower part 3 in relation to one another or in space, the angular velocities or the walking speed, in order to limit the power output and additionally control the time sequence of the release of energy. By relaxing the spring 54 it is possible to introduce less energy into the joint device 1; by pretensioning the spring 54, it is possible to maintain assistance of the flexion over a longer time period and over a greater flexion angle, in order to achieve the desired harmonious gait pattern.

A variant of the invention is shown in FIG. 11, one in which a displacement at the distal mounting point takes place instead of the relaxing or compressing of the spring 54 substantially in its longitudinal extent. The upper fastening point is guided in a displaceable spring attachment 25, which by way of the actuator 10 is displaceable back and forth in the direction of the double-headed arrow. Depending on the point of articulation and the direction of movement, the elastic cord 54 is tensioned or relaxed. Both in FIG. 10 and in FIG. 11, the energy from the extension movement is stored in the elastic cord 54. After ending of the extension movement, it is possible that the motor 10 can subsequently retension the cord 54 if the expected energy to be applied is not sufficient to bring about desired assistance in the initiation of flexion. The pretensioning advantageously takes place whenever the joint device 1 is in a completely extended state, in order to have to work as little as possible against a pretensioning movement. It is possible by the adjustment either of the pretensioning of the elastic cord 54 or of the proximal mounting position to set the stretching angle from which the conversion device 5 becomes active, whereby how much energy is to be stored in the energy store 5 can also be set.

Figure 12:
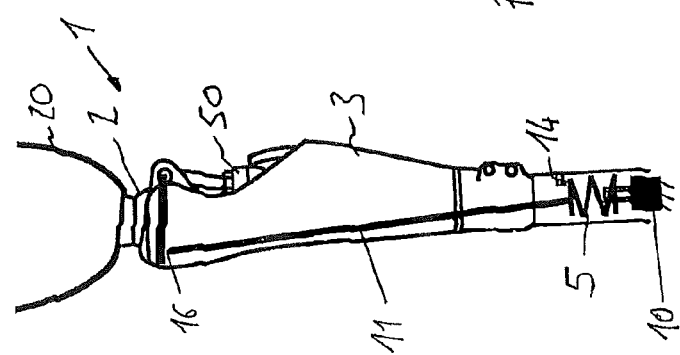
FIG. 12 shows a variant with a spring arranged in the lower part.

In FIG. 12, a variant of the joint device 1 is shown, one in which the conversion device 5 in the form of the spring 54 is arranged in the lower leg tube. The actuator 10 is connected to the spring 5 and can either compress it or wind it up, depending on the configuration of the spring as a compression spring or a spiral spring. The spring 5 is coupled by way of a thrust rod 11 to a limit stop 16, which is fastened to the upper part 2. By activation of the motor 10, the bottom point of the spring 5 can be changed, whereby the thrust rod 11 can be used to set when the spring 5 comes into contact with the limit stop 16. The earlier the thrust rod 11 comes into contact with the limit stop 16, the greater the path of adjustment and the compression of the spring 5, so that correspondingly more energy is stored in the spring 5. Accordingly, when it is converted back, more energy is transmitted from the spring by way of the thrust rod 11 to the limit stop 16, so that increased flexion assistance can be achieved. In order to influence the release of energy, the spring 5 is either compressed or relaxed in the event of movement assistance.

Figure 13:
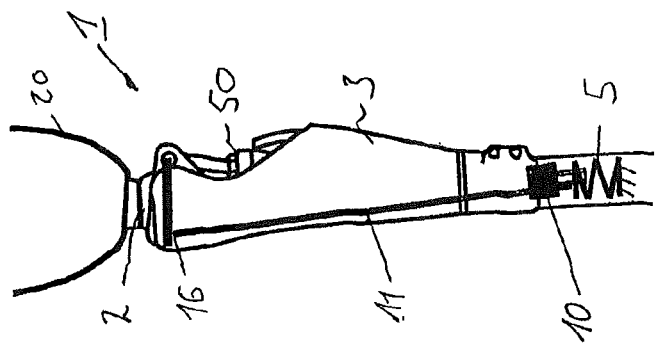
FIG. 13 shows a variant of FIG. 3 with an interposed actuator.

In FIG. 13 there is shown a variant that corresponds substantially to FIG. 12; however, the actuator 10, possibly with a spindle drive and freewheeling in one direction, is arranged between the spring 5 and the thrust rod 10, so that the bottom point of the spring 5 remains fixed, but the spring 5 can be precompressed with the motor 10. If flexion assistance is initiated, the motor 10 must join in the rotation, in order to release the energy and transmit it by way of the thrust rod 11 and the stop limit 16 to the joint device, whereby particularly good control over the release of energy can be achieved. It is similarly possible to stop the release of energy, which may be advisable if a situation has been misjudged.

Figure 14:
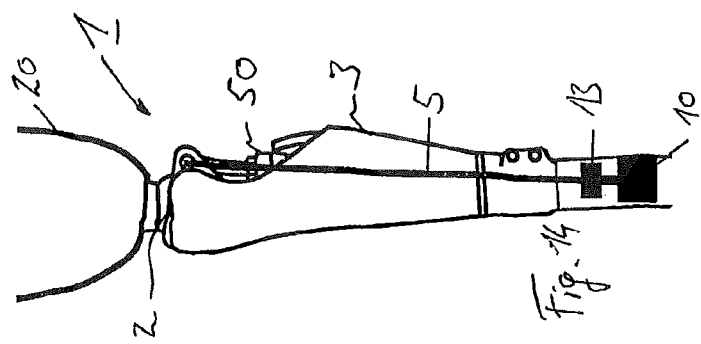
FIG. 14 shows a variant with a twisted filament as an energy store.

In FIG. 14, a twisted filament is shown as the energy store 54 and conversion device 5, in the case of which shortening is achieved by a twisting of filaments. By increasing or decreasing the twisting, the contact point from which the twisted filament builds up tensile forces can be set. Between the motor 10 and the twisted filament 54, an axial decoupling 13 is provided.

Apart from the embodiment shown of the energy store as a spring, by using a transmission gear mechanism and a generator it may possibly also be designed as an electrical energy store in the form of a battery, a storage battery or a capacitor. For converting the stored electrical energy back, the generator is switched as a motor, so that driving and assistance of the relative displacement of the lower part 3 in relation to the upper part 2 can take place. To increase the amount of energy, a generator may be assigned to the electrical energy store; it is similarly possible to provide a further energy store, which serves as a buffer into which excess electrical energy is fed or from which energy that is additionally required is provided.

The springs as energy stores 54 may be designed as tension springs, compression springs, torsion springs or elastomer elements, which from a certain stretching angle, which is set by the actuator 10, come into contact and from this point in time both convert mechanical work into energy and feed it back for movement assistance. The spring in this case takes up the energy from the movement in the direction of extension, and serves at the same time as a decelerating device and extension stop limit. With the initiation of the swinging phase, the energy is released again and helps the user to initiate the swinging phase. The actuator 10 can be used to adjust the point in time of the contact of the spring in the case of the release of energy, so that different, controlled forms of assistance are possible for different walking speeds. It is similarly possible that the respective spring is recompressed by way of the motor 10, if the energy stored by the preceding movement is not sufficient to provide sufficient assistance; for example, in the case of particularly slow walking or going down steps, the mechanical work may not be sufficient to compress the spring sufficiently. As shown in FIG. 12, the spring 5 may be assigned a releasing device 14, by way of which the initiating time for the release of the stored energy can be additionally ensured.

In order to ensure the initiation of the release, the joint device 1 may include a safety device, which is formed by the hydraulics in the damper 50 or by a control of the motor 10, which ensure that the spring energy applied is reduced again in time.

On account of the fact that the kinetic energy in the extension is at least partially stored, the assistance provided by the motor can operate very sparingly. The battery for the actuator 10 can be made small and lightweight, as can the actuator 10 itself, since the actuator 10 has sufficient time when retensioning in the standing phase to compress the spring, and the feeding in of the energy does not have to take place as quickly as the release for the initiation of the swinging phase. The motor 10 controls the release of energy from the spring, possibly in conjunction with the separate damper 20. The flexion assistance provided by the energy store helps in achieving the necessary bending angle in the case of alternating climbing up stairs and when overcoming obstacles, and saves hip work.

Figure 15:
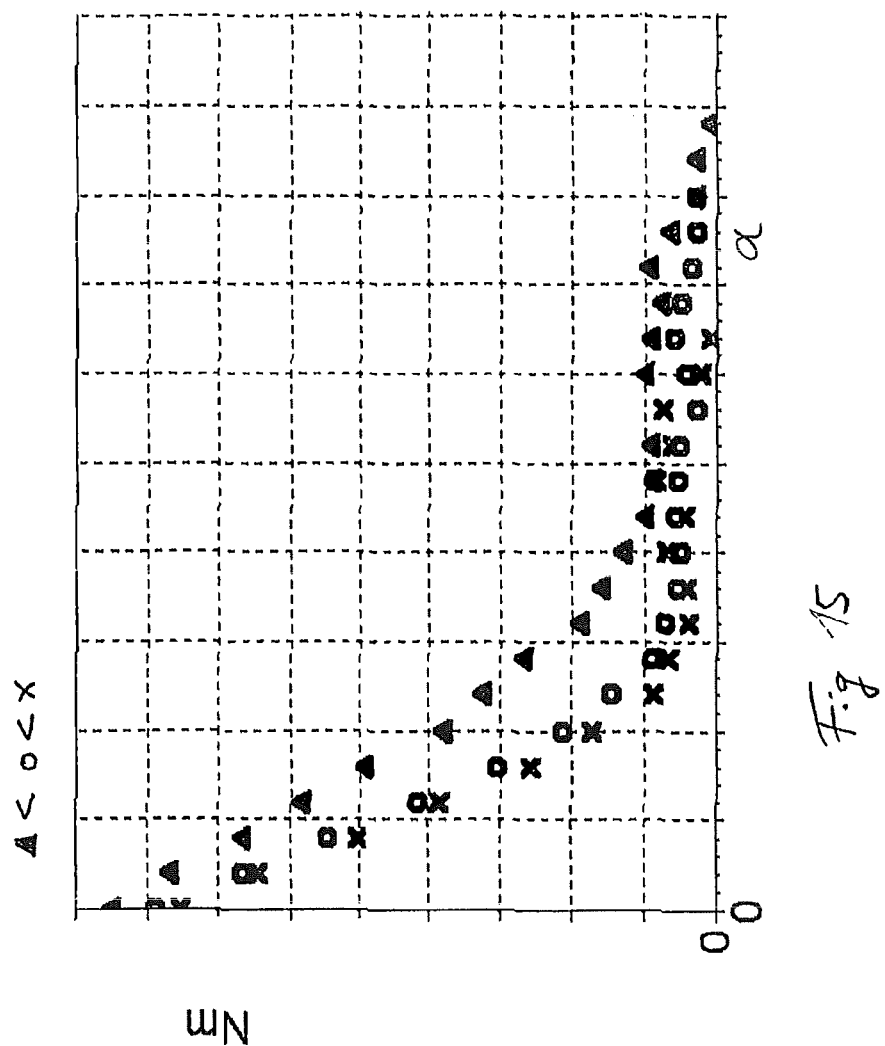
FIG. 15 shows a representation of drive moment progressions for different walking speeds.

In FIG. 15, the drive moment for different walking speeds are shown against the joint angle α. The representation is for three different walking speeds, the respective walking speeds being represented by different symbols in the diagram; the lowest walking speed is identified by a triangle, the medium walking speed by a circle and the highest walking speed by an X. The drive moment is the effective drive moment in Nm, that is to say the energy stored by the storage device 5 and fed back, less the losses such as damping or friction. It is evident that initially a very high drive moment is used in order to be able to provide the flexion assistance at the beginning. With an increasing joint angle α, here the knee angle, which is measured from a maximum extension position, the drive moment to be applied initially falls steeply, remains constant over a small angular range, briefly rises again and then, up to maximum flexion, falls to zero. It is evident that the flexion assistance at low walking speeds, represented by the triangle, is greater than at high walking speeds. The drive moment progression, as it is shown in FIG. 15, cannot be produced by recompressing or relaxing a spring without the influence of a motor, since, according to the invention, after a strong drop in the drive moment, the moment is maintained over a further time period up until reaching the maximum angle.

Figure 16:
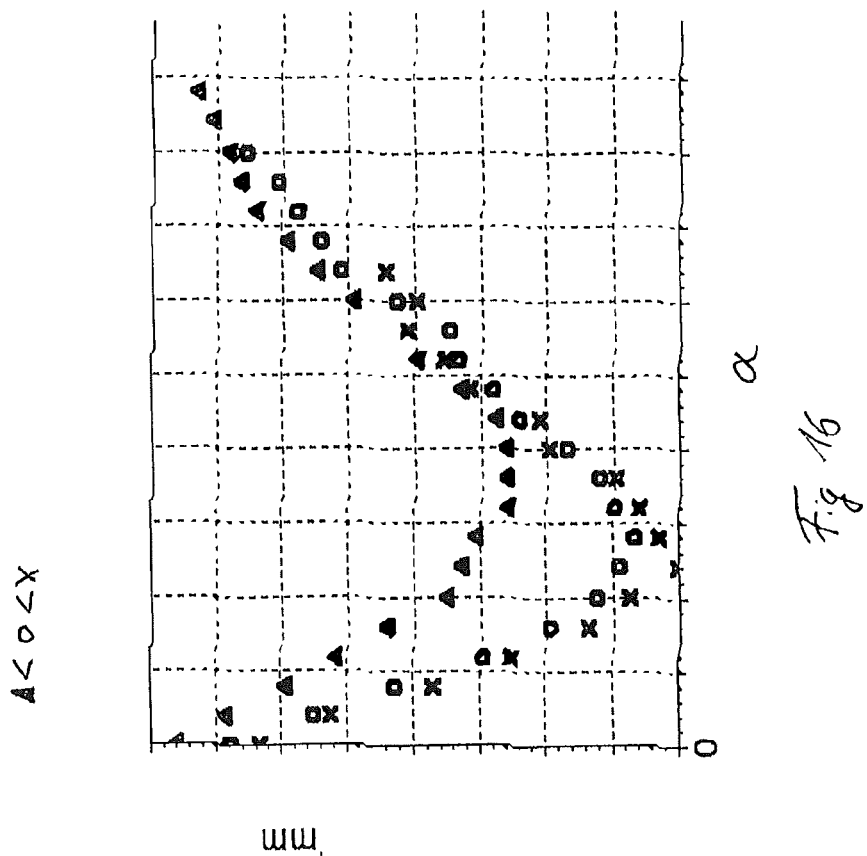
FIG. 16 shows a representation of different paths of displacement against a joint angle for various walking speeds.
Figure 14:
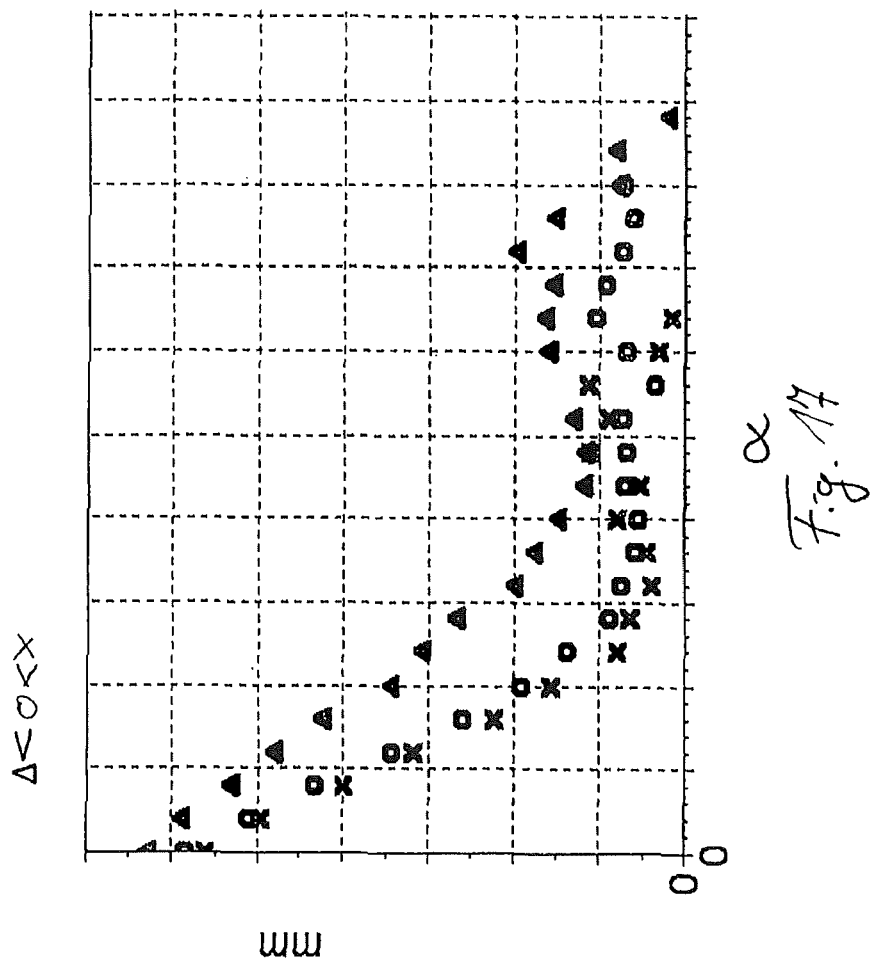

FIG. 16 shows a diagram in which the tension path of the motor 10 is plotted against the joint angle α. Various walking speeds are presented, once again identified by a triangle, a circle and an X; the lowest walking speed is represented by a triangle. The representation relates to the translational movement of the motor 10 in the case of the embodiments of FIGS. 10, 12 and 14. The path of displacement according to FIG. 16 is adjusted such that the drive moment curve according to FIG. 15 can be achieved. The respective progression is different for each spring chosen and, depending on the property of the spring, can lead to a greater or smaller path of displacement. The aim is to achieve a displacement, and consequently compressing, of the spring that is as small as possible. At the start of the initiation of bending, it is evident that the motor allows the spring to slide back, in order to achieve the fastest possible force reduction, in order that the feeling of controlled flexion continues to be maintained. At greater angles, the spring is compressed again, in order to maintain the force or increase it again. Here, too, it is significant that, at slower walking speeds, increased assistance is necessary. The release of the spring, and consequently of the energy, for flexion assistance and the driving of the motor take place at the same time, so that it is possible to keep a check over the entire progression of the flexion assistance.

FIG. 17 shows the changing of the lever arm according to an embodiment of FIG. 11 against the joint angle α for different walking speeds. Here, too, at the same time as the release of the spring the motor 10 is activated, in order to adjust the lever arm. Initially, the lever arm is quickly reduced, in order to bring about a reduction in the force; subsequently, the lever arm is increased again, in order to apply force and assist the flexion movement over a greater angular range a.

Figure 18:
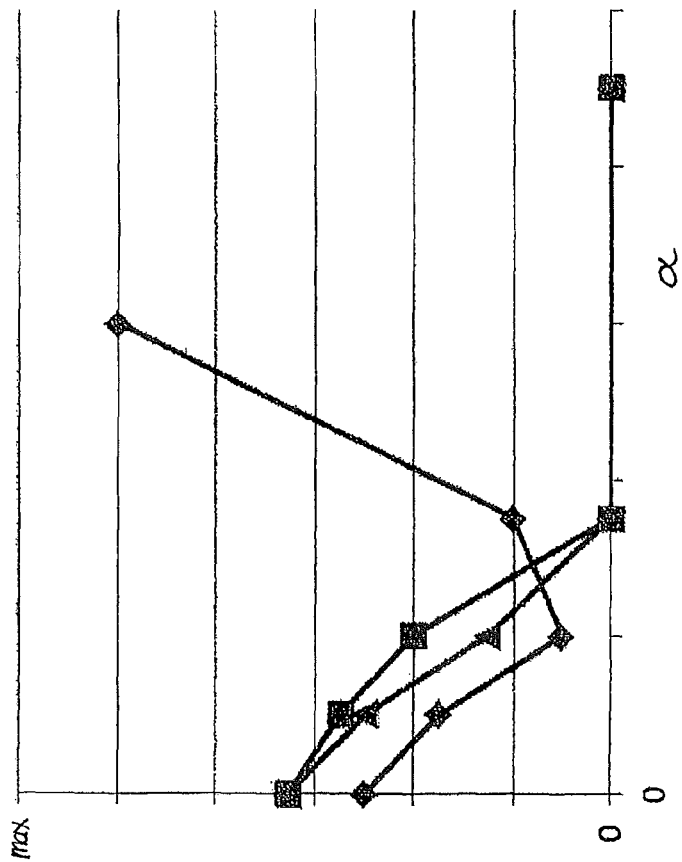
FIG. 18 shows a representation of a flexion damping setting of a damper against a knee angle.

In FIG. 18, the flexion damping setting of the damper device 50 is shown against the joint angle α for various speeds. As a departure from the previous figures, the lowest walking speed is identified by a square, the medium speed by a triangle and the highest walking speed by a rhomboid. A medium flexion damping setting of the damper device 50 is initially provided, decreasing as the joint angle α increases. At high walking speeds, raising of the flexion damping may take place toward the end of the swinging phase, in order to avoid excessive bending of the lower part 3. By changing the flexion damping setting in the damper unit 50, it is possible in conjunction with the motor control to carry out effective and safe, as well as simple, control of the introduction of energy for movement assistance.

Apart from the embodiment shown as flexion assistance, the device may in principle also be used for extension assistance; the statements made in relation to flexion assistance also apply correspondingly to extension assistance, it also being possible and intended that flexion assistance and extension assistance are arranged together in a joint device.

The invention claimed is:

1. A method for controlling an orthopedic joint device of a lower extremity, the orthopedic joint device having an upper part and a lower part mounted in an articulated manner thereon, the method comprising:
   providing an energy conversion device arranged between the upper part and the lower part, the energy conversion device comprising a hydraulic cylinder, a spring, and a piston arranged on a piston rod, the piston separating the hydraulic cylinder into an upper chamber and a lower chamber, the spring arranged within the lower chamber;
   converting and storing kinetic energy from relative movement between the lower part and the upper part with the energy conversion device; and
   feeding back the kinetic energy to the orthopedic joint device with the energy conversion device after extension during a stance phase and only during the stance phase to assist with a flexion movement of the lower part relative to the upper part;
   wherein within a movement cycle, the kinetic energy is converted and stored and, within the same movement cycle, is fed back to the orthopedic joint device in a controlled manner after a time delay such that the energy feedback does not occur immediately after converting and storing of the kinetic energy.

2. The method as claimed in claim 1, wherein the kinetic energy is converted and stored during an extension movement of the orthopedic joint device.

3. The method as claimed in claim 2, wherein the kinetic energy is at least one of converted and stored before reaching a stretching stop limit and is fed back to initiate and assist the flexion movement of the orthopedic joint device.

4. The method as claimed in claim 1, wherein the kinetic energy is stored during the stance phase at a beginning of the flexion movement with heel loading.

5. The method as claimed in claim 4, wherein the kinetic energy is converted and stored with an initial heel impact and fed back as part of at least one of initiating and assisting the flexion movement of the orthopedic joint device.

6. The method as claimed in claim 1, wherein, with increasing walking speed, less of the kinetic energy is supplied to the orthopedic joint device.

7. The method as claimed in claim 1, wherein the converted kinetic energy is completely fed back to the orthopedic joint device in the movement cycle.

8. The method as claimed in claim 1, wherein the kinetic energy fed back is dependent upon at least one of the following criterion:
   an angular position of the upper part in relation to the lower part,
   a position of at least one of the upper part and the lower part in space,
   an angular velocity of at least one of the upper part and the lower part,
   a relative velocity between the upper part and the lower part,
   a loading situation, and
   an acceleration of at least one of the upper part and the lower part.

9. The method as claimed in claim 8, wherein the kinetic energy is stored with the spring and is fed back from the spring dependent upon at least one of the criterion recited in claim 8.

10. A method for controlling an orthopedic joint device of a lower extremity, the orthopedic joint device having an upper part and a lower part mounted in an articulated manner thereon, the method comprising:
   providing an energy conversion device arranged between the upper part and the lower part, the energy conversion device comprising a hydraulic cylinder, a spring, and a piston arranged on a piston rod, the piston separating the hydraulic cylinder into upper and lower chambers, the lower chamber increasing in volume during a flexion movement of the lower part relative to the upper part, the spring being arranged within the lower chamber;
   converting and storing kinetic energy from relative movement between the lower part and the upper part with the energy conversion device; and
   feeding back the kinetic energy to the orthopedic joint device with the energy conversion device after extension during a stance phase and only during the stance phase to assist with the flexion movement of the lower part relative to the upper part;
   wherein within a movement cycle, the kinetic energy is converted and stored and, within the same movement cycle, is fed back to the orthopedic joint device in a controlled manner after a time delay such that the energy feedback does not occur immediately after converting and storing of the kinetic energy.

* * * * *